(12) United States Patent
Spreiter et al.

(10) Patent No.: US 11,325,231 B2
(45) Date of Patent: May 10, 2022

(54) SELF-RETAINING SCREWDRIVER WITH ENGAGING TIP FEATURE

(71) Applicant: DEPUY SYNTHES PRODUCTS, INC., Raynham, MA (US)

(72) Inventors: Gregor Spreiter, Solothurn (CH); Yvonne Schumacher, Solothurn (CH); Simon Scherrer, Zurich (CH); Henri Défossez, Neuchatel (CH); Joshua McManus, Downingtown, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 355 days.

(21) Appl. No.: 16/692,070

(22) Filed: Nov. 22, 2019

(65) Prior Publication Data

US 2021/0154811 A1     May 27, 2021

(51) Int. Cl.
    *B25B 23/00*       (2006.01)
    *B25B 15/02*       (2006.01)

(52) U.S. Cl.
    CPC .......... *B25B 23/0042* (2013.01); *B25B 15/02* (2013.01); *B25B 23/0021* (2013.01)

(58) Field of Classification Search
    CPC ..... A61C 8/0089; B25B 15/02; B25B 23/005; A61B 17/88; A61B 17/888; A61B 17/8615; A61B 17/8888
See application file for complete search history.

(56) References Cited

U.S. PATENT DOCUMENTS

| | | | | |
|---|---|---|---|---|
| 2,276,470 A | * | 3/1942 | Dodelin | ................ B25B 23/005 81/451 |
| 2,637,229 A | * | 5/1953 | Lee | ........................ B25B 23/101 81/451 |
| 4,221,249 A | | 9/1980 | Mazzeo et al. | |
| 4,704,929 A | | 11/1987 | Osada | |
| 5,129,292 A | | 7/1992 | Albert | |
| 6,328,746 B1 | | 12/2001 | Gambale | |
| 6,904,836 B1 | * | 6/2005 | Andrei | ..................... B25B 15/02 81/444 |
| 7,137,766 B2 | | 11/2006 | Weinstein et al. | |
| 7,287,452 B1 | | 10/2007 | Tsai | |
| 7,650,991 B2 | | 1/2010 | Hester et al. | |
| 7,757,590 B2 | | 7/2010 | Swartz | |
| 8,172,886 B2 | | 5/2012 | Castaneda et al. | |
| 8,414,594 B2 | | 4/2013 | Berger et al. | |
| 8,460,306 B2 | * | 6/2013 | Schaffran | ............. A61C 8/0089 606/104 |
| 8,726,769 B1 | | 5/2014 | Jacker | |
| 9,907,576 B2 | * | 3/2018 | Mahajan | ............ A61B 17/7032 |

(Continued)

*Primary Examiner* — David B. Thomas
(74) *Attorney, Agent, or Firm* — Fay Kaplun & Marcin, LLP (57) ABSTRACT

A screwdriver assembly includes a screwdriver shaft and an insert. The screwdriver shaft extends longitudinally from a proximal end to a distal end and having a longitudinal channel extending therethrough. The insert has a longitudinal shaft received within the longitudinal channel and a distal end extending distally relative to the distal end of the screwdriver shaft. The insert shaft is rotatable relative to the screwdriver shaft. The distal end of the insert is sized and shaped to engage a head of a screw. The distal end of the insert is disengaged from the screw head by rotating the insert relative to the screwdriver shaft.

20 Claims, 5 Drawing Sheets

(56) References Cited

U.S. PATENT DOCUMENTS

| | | | | |
|---|---|---|---|---|
| 10,426,535 B2 * | 10/2019 | Zander | ............... | A61B 17/862 |
| 10,531,905 B2 * | 1/2020 | Gault | ............... | A61B 17/8635 |
| 10,835,299 B2 * | 11/2020 | Petit | ............... | A61B 17/8888 |
| 11,026,736 B2 * | 6/2021 | Rohlfing | ............ | A61B 17/7082 |
| 11,058,469 B2 * | 7/2021 | Mahajan | ............ | A61B 17/8605 |
| 2016/0199967 A1 * | 7/2016 | Stahl | ............... | B25B 23/12 |
| | | | | 81/460 |
| 2017/0086966 A1 * | 3/2017 | Spenciner | ............ | A61B 17/8863 |
| 2017/0231675 A1 * | 8/2017 | Combrowski | ............ | A61B 17/864 |
| | | | | 606/305 |

* cited by examiner

SELF-RETAINING SCREWDRIVER WITH ENGAGING TIP FEATURE

FIELD OF INVENTION

The present invention relates generally to a screwdriver assembly with a self-retaining tip and a release mechanism.

BACKGROUND

A screw may disengage from a screwdriver during the insertion of the screw into a target site. For example, an intramedullary nail screw may detach from a self-retaining screwdriver while the physician is guiding the screw into the predrilled hole in the bone, causing the screw to fall to the floor, get lost in the soft tissues of the patient, or otherwise land outside the sterile field. The problem of retaining the screw on the screwdriver is currently addressed with various hardware including a conical screwdriver tip for gradual interference, a clamp mechanism on the screwdriver to hold the screw, a sliding shaft on the screwdriver to force interference, and threaded connections to the screw and the screwdriver. However, the existing solutions can add significant cost and complexity to the fixing of a screw to a target anatomy or an implant.

SUMMARY

The present disclosure relates to a screwdriver assembly includes a screwdriver shaft and an insert. The screwdriver shaft extends longitudinally from a proximal end to a distal end and having a longitudinal channel extending therethrough. The insert has a longitudinal shaft received within the longitudinal channel and a distal end extending distally relative to the distal end of the screwdriver shaft. The insert shaft is rotatable relative to the screwdriver shaft. The distal end of the insert is sized and shaped to engage a head of a screw. The distal end of the insert is disengaged from the screw head by rotating the insert relative to the screwdriver shaft.

In an embodiment, the distal end of the insert is a deformable tip, a cross-section of the deformable tip being larger than a cross-section of the longitudinal shaft of the insert.

In an embodiment, the deformable tip has a slot facilitating compression of the deformable tip until a cross-section thereof is at least as small as the cross-section of the longitudinal shaft of the insert.

In an embodiment, the head of the screw further comprises a cavity, the cavity having a proximal-most portion, an intermediate portion, and a distal-most portion.

In an embodiment, the proximal-most portion of the cavity is sized and shaped to receive the distal end of the insert, the intermediate portion of the cavity is sized and shaped to receive the longitudinal shaft of the insert, and the distal-most portion of the cavity is sized and shaped to receive the distal end of the screwdriver.

In an embodiment, the screwdriver assembly further includes a snap lock between the distal end of the insert and the intermediate portion of the cavity to temporarily prevent extraction of the screwdriver from the screw.

In an embodiment, the screwdriver assembly further includes a first threaded portion on a proximal portion of the longitudinal channel of the screwdriver; and a second threaded portion on a proximal portion of the longitudinal shaft of the insert. The first threaded portion is complementary to the second threaded portion.

In an embodiment, the head of the screw further comprises a proximal recessed portion sized and shaped to receive the distal end of the insert; and a distal recessed portion sized and shaped to receive the distal end of the screwdriver.

In an embodiment, the distal end of the screwdriver has a hexagonal shaped cross-section, ion, the cross-section corresponding to a plurality of ridges in the proximal recessed portion.

The present disclosure also relates to a screwdriver assembly which includes a sleeve with a ridged proximal end and an internally threaded distal end; a screwdriver having a distal end engageable with the ridged proximal end of the sleeve; and a screw with an externally threaded head engageable with the distal end of the sleeve, rotation of the assembly inserting the screw into a target hole while the sleeve remains external to the target hole, the rotation of the assembly unthreading the sleeve from the screw so that, when the screw is disengaged from the sleeve, the sleeve remains engaged with the screwdriver and is withdrawn therewith.

In an embodiment, the sleeve is formed from a flexible material that may elastically deform from an applied force.

In an embodiment, the screw has a threading extending from a distal end of the threaded head to a distal end of the screw, wherein a length of the externally threaded head corresponds to a length of the threading on the screw.

In addition, the present disclosure relates to a screwdriver assembly which includes a screwdriver shaft and a screw being formed as a unified piece having an interface therebetween, the interface having a reduced diameter relative to the shaft and the screw; an a sleeve coupled to the screwdriver shaft at a handle, the screwdriver shaft being rotatable relative to the sleeve to insert the screw into a target hole, the sleeve remaining external to the target hole, rotation of the screwdriver stressing the interface so that the interface breaks when the screw has been inserted into the target hole to a target depth.

In an embodiment, the sleeve is removably coupleable to the handle, at least one of the sleeve and the handle being reusable.

In an embodiment, the interface has a shape that creates a stress riser to initiate the interface break between the screw and the shaft.

Furthermore, the present disclosure relates to a method which includes inserting a distal end of a screw an initial distance into a target hole in bone, a head of the screw being releasably coupled to a screwdriver, the screwdriver being releasably coupled to a sleeve; rotating the screwdriver until a distal end of the sleeve engages a surface of the bone surrounding the target hole, preventing the sleeve from rotating with the screw; advancing the screw distally into the target hole until the screw is completely countersunk into the target hole, disengaging the sleeve from the screw; interference between the bone and the sleeve prevents rotation of the sleeve until the screwdriver disengages from the screw; and withdrawing the screwdriver and the sleeve from the hone.

In an embodiment, a breakable interface connects a distal end of the screwdriver to the head of the screw, further comprising disengaging the screwdriver from the screw by breaking the interface.

Also, the present disclosure relates to a method which includes inserting a rotatable insert into a channel extending longitudinally through a screwdriver, a distal end of the insert extending past a distal end of the screwdriver; advancing the distal end of the insert and the distal end of the screwdriver into a head of a screw; inserting a distal end of the screw an initial distance into a target hole in bone; rotating the insert relative to the screwdriver to advance the screw distally into the target hole; disengaging the distal end of the screwdriver and the distal end of the insert from the screw; and withdrawing the screwdriver and the insert from the bone.

In an embodiment, the insert remains in a fixed position relative to the screw when the insert is rotated relative to the screwdriver.

In an embodiment, the method further includes rotating the insert a predetermined amount in a first direction to prevent separation of the screwdriver and the screw; advancing the screw distally by rotating the screwdriver; and rotating the insert the predetermined amount in a second direction, the second direction being opposite of the first direction, to allow separation of the screwdriver from the screw.

BRIEF DESCRIPTION

DETAILED DESCRIPTION

The present disclosure may be further understood with reference to the following description and the appended drawings, wherein like elements are referred to with the same reference numerals. The exemplary embodiments describe self-retaining screws and screwdriver devices having mechanisms for attaching the screws to and detaching the screws from the screwdrivers. The devices are configured for a reliable attachment during the insertion of the screw and a simple release mechanism actuated by a rotating aspect of the screwdriver, facilitating ease of use for the physician. It should be noted that the terms "proximal" and "distal," as used herein are intended to refer to a direction toward (proximal) and away from (distal) a user of the device.

FIGS. 1-4 show a screwdriver assembly 100 having a threaded sleeve 110 removably attachable to both a head 104 of a screw 102 and a conical head 122 of a screwdriver 120 to maintain a connection therebetween during the insertion of the screw 102 into a target hole. The sleeve 110 is configured to decouple from the screw 102 after the screw 102 has been inserted into the target hole as desired. The sleeve 110 is then withdrawn along with the screwdriver 120, in a manner to be described in detail below.

The sleeve 110 has a distal end 112 with a threaded interior surface that may be assembled with, i.e. threaded onto, a complementary threading on a threaded exterior of the head 104 of the screw 102. The screw 102 in this example is counter-sinkable, with the threaded head 104 having a tapered distal end and a smaller diameter shaft 108 extending distally therefrom. The proximal end of the head 104 has a recess 106 sized and shaped for receiving the distal tip 124 of the screwdriver 120. The recess 106 may be shaped in any suitable manner known in the art (i.e., complementarily shaped with respect to the distal tip 124) so that torque from the screwdriver 120 may be transferred to the screw 102. In the embodiment shown in FIG. 1, the screw 102 has a recess 106 formed as a hexagonal socket configured to receive a correspondingly sized and shaped hexagonal tip 124 of the screwdriver 120.

Figure 1:
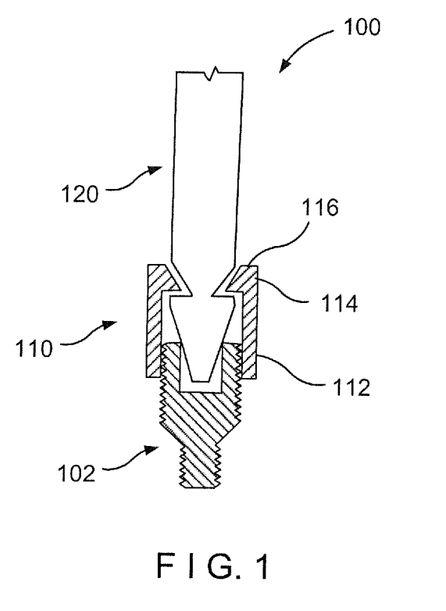
FIG. 1 shows a screwdriver assembly having a threaded sleeve removably attachable to both a head of a screw and a conical head of a screwdriver according to a first exemplary embodiment.
Figure 2:
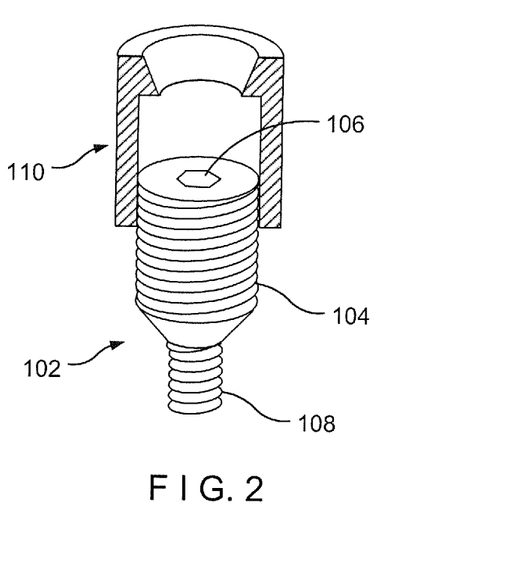
FIG. 2 shows the attached sleeve and screw of the assembly of FIG. 1.
Figure 3:
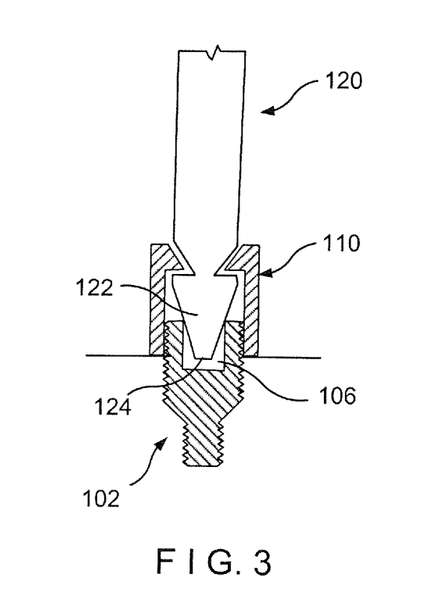
FIG. 3 shows the assembly of FIG. 1 contacting a target surface.
Figure 4:
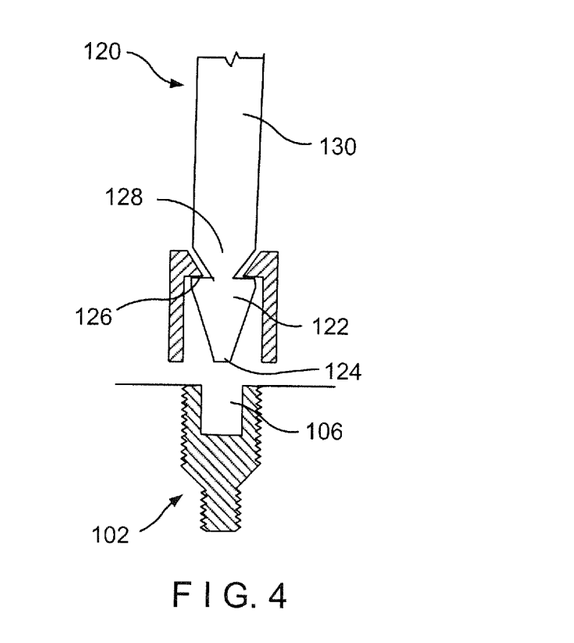
FIG. 4 shows the screwdriver and sleeve of the assembly of FIG. 1 being withdrawn from the implanted screw.

The sleeve 110 may be pre-assembled with the screw 102 and packaged therewith. In any case, when ready for insertion into a target hole, the distal end 112 of the sleeve 110 is threaded onto the head 104 of the screw 102 to assemble the two elements. The proximal end 114 of the sleeve 110 has a ridge 116 extending radially inward from its inner diameter, the ridge 116 having a triangular cross section and being sized and shaped to fit within a correspondingly shaped cavity 126 in the screwdriver 120.

The screwdriver 120 has a conical head 122 with a distal tip 124 sized to engage the recess 106 on the head 104 of the screw 102. The conical head 122 increases in diameter from the distal tip 124 to a proximal end having a diameter substantially corresponding to the inner diameter of the sleeve 110. When the head 122 of the screwdriver 120 is inserted in the sleeve 110, with the screw 102 and the sleeve 110 preassembled, i.e. fully threaded together, the head 122 fits snuggly within the cavity defined by the ridge 116, the interior diameter of the sleeve 110 and the screw 102, as shown in FIG. 1. The screwdriver 120 has a shaft 130 proximal to the head 122 with a neck portion 128 having a conical profile and defining a cavity 126 between the shaft 130 and the head 122, the cavity 126 being sized and shaped to engage the ridge 116 of the sleeve 110 when the head 122 of the screwdriver 120 is assembled with, i.e. fitted into, the sleeve 110.

The sleeve 110 in this embodiment is formed from a flexible material such as plastic, or another similarly flexible material, that may elastically deform when subjected to the forces to which it is subjected as the screwdriver head 122 is inserted therein. The screwdriver head 122 is fitted into the sleeve 110 by, for example, manually pushing the conical distal tip of the head 122 into the proximal opening of the sleeve 110 past the ridge 116, which stretches radially outward under the pressure as the increasing diameter of the conical head 122 passes through the proximal opening in the sleeve 110. When the ridge 116 reaches the cavity 126, the ridge 116 snaps radially inward to attach the sleeve 110 to the screwdriver 120.

Figure 5:
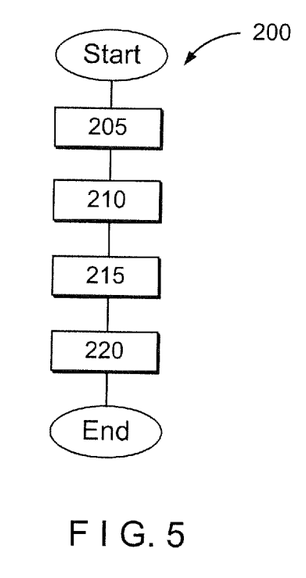
FIG. 5 shows a method for inserting the screw and releasing the sleeve therefrom with the screwdriver assembly of FIG. 1.

The assembled device 100 then includes the screwdriver 120 inserted into the proximal end of the screw 102 that is held in position relative to the screwdriver 120 via the threaded connection to the sleeve 110 that is clipped to the screwdriver 120. This assembled device may then be used to insert the screw 102, e.g. an IM nail screw, into a target hole, e.g. a pre-drilled hole in a bone. FIG. 5 shows a method 200 for inserting a screw and releasing the sleeve therefrom, whereby the release mechanism will be described.

In 205, the distal end of the screw 102 is engaged with the target hole and screwed an initial distance thereinto. The target hole in this example has a diameter substantially corresponding to the diameter of the shaft 108 of the screw 102. In 210, as the screw 102 is screwed into the target hole, the distal end 112 of the sleeve 110 approaches and engages the surface of the material, e.g. bone, surrounding the target hole. In other words, the ringed diameter of the sleeve 110 is brought into contact with the bone surface, which frictionally engages the sleeve 110 thereby preventing the sleeve 110 from rotating as the screw 102 is screwed further distally into the target hole. Thus, as the physician continues rotating the screw 102 after the sleeve 110 and the bone surface are engaged, the sleeve 110 stops rotating and the screw 102 rotates within the sleeve 110 until the screw 102 is completely uncoupled from the sleeve 110. The distal end of the screw 102, i.e., the end of the screw 102 inserted into the target hole, may be threaded, such that as the screw 102 is screwed into the bone, an added resistance from the screw threads will indicate to the user that the screw 102 is nearly fully screwed into the bone.

In 215, the screw 102 is advanced sufficiently distally into the target hole that the screw 102 is completely countersunk into the target hole and completely unthreaded from the sleeve 110. A length of the threaded connection between the screw 102 and the sleeve 110 may correspond to a length of the threading of the distal end of the screw 102, such that when the head 104 is flush with the bone, the screw 102 is disengaged from the sleeve 110. The sleeve 110 is under its greatest compressive force when the screw 102 is fully inserted, considering the distal distance the screwdriver 120 has advanced while advancing the screw 102 into the bone and unthreading the screw 102 from the sleeve 110, while the sleeve 110 is prevented from further distal movement by the material surface. In 220, once the sleeve 110 and the screw 102 are fully disengaged, the screwdriver 120 is withdrawn proximally and the axial compression is relieved. The ridge 116 on the proximal end 114 of the sleeve 110 remains engaged in the cavity 126 of the screwdriver 120, and both the screwdriver 120 and the sleeve 110 may be withdrawn fully from the body.

Thus, the assembly 100 utilizes a passive mechanism to engage and disengage the screw 102 from the sleeve 110 and provides a simple attachment mechanism for the screw 102 and the screwdriver 120, and an automatic disengagement mechanism between the screw 102 and the screwdriver 120 once the screw 102 has been inserted to its proper depth. In other words, once the sleeve 110 and the screw 102 are disengaged, the screwdriver 120 is disengaged from the screw 102, thus the user does not need to make any additional actions besides attaching the screw 102 to the screwdriver 120.

Figure 6:
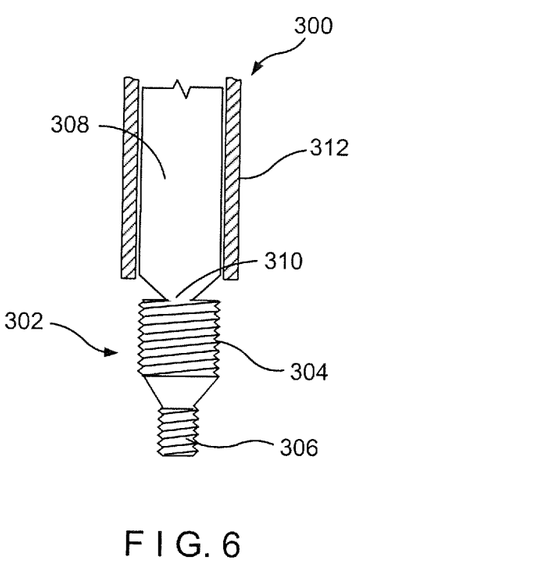
FIG. 6 shows a screwdriver assembly including a screw and a screwdriver shaft formed as a unified piece and having a breakable interface therebetween according to a second exemplary embodiment.
Figure 7:
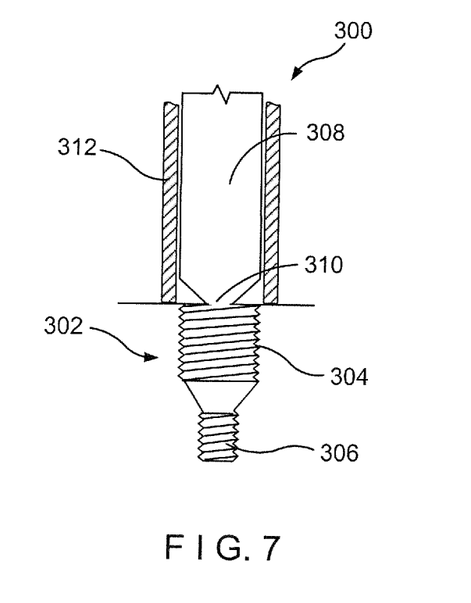
FIG. 7 shows the assembly of FIG. 6 contacting a target surface.
Figure 8:
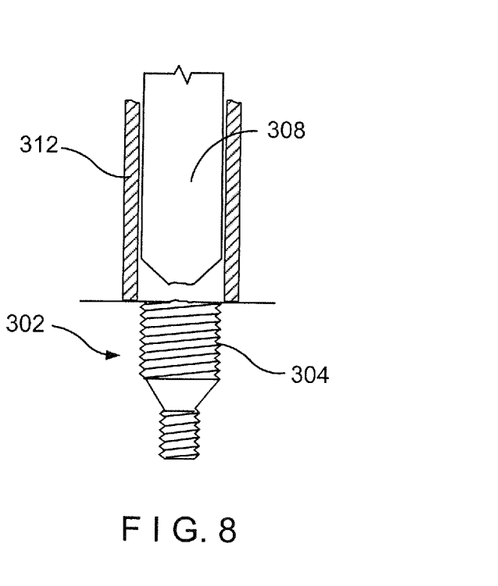
FIG. 8 shows the assembly of FIG. 6 wherein the screw is disconnected from the screwdriver due to the breakable interface breaking from an applied torque.

In an alternate embodiment, as shown in FIGS. 6-8, a screwdriver assembly 300 includes a screw 302 and a screwdriver shaft 308 formed as a unitary piece with the screwdriver shaft 308 being connected to the screw 302 via a breakable interface 310. The screwdriver shaft 308 has a proximal portion fixable to a handle (not shown) of a sleeve 312. As would be understood by those skilled in the art the handle may be fixed to the sleeve 312 in any manner. For example, as the screwdriver shaft 308 is severed from the screw 302 during use, the screwdriver shaft 308 may be formed as a one-time use item that is removably coupleable to a reusable handle and the sleeve 312 may be formed as a one-time use item permanently, but rotatably coupled to the shaft 308. Alternatively, the sleeve 312 may be a re-usable item removable from the shaft 308 and, after attachable to a subsequent shaft 308 if desired.

The screw portion 302 of this embodiment the unified piece has a counter-sinkable head 304 and a shaft 306, with a tapered profile similar to that of the screw 102 described with respect to FIG. 1. However, the screw head 304 does not have an exterior thread. The interface 310 between the screw 302 and the screwdriver shaft 308 is a recessed portion with a conical shape although those skilled in the art will understand that this interface 310 may take any desired shape so long as, when the screw 302 is separated from the shaft 308 as described below, the proximal end of the head of the screw 302 takes on a desired shape and desired surface properties. The shape of the interface 310 creates a stress riser to initiate a separation between the screw 302 and the screwdriver shaft 308. The screw 302 and the screwdriver shaft 308 may have a similar diameter on opposing sides of the interface 310, although this is not required. The interface 310, with its diameter smaller than that of the screw 302 and the shaft 308 forms a weakened section of the device 300 that will break when torqued as described below.

The assembly 300 is configured so that, as the screw 302 is screwed into the hone, the distal end of the sleeve 312 is brought into contact with the bone surrounding the head of the screw 302 and, as the screw 302 is further advanced into the bone, the compressive force exerted on the sleeve 312 by the user increases a frictional force resisting the rotation of the sleeve 312 over the bone until the sleeve 312 no longer rotates. At this point, as the screw 302 rotates within the sleeve and, as the screw becomes seated in the bone, the torque applied between the screw 302 and the shaft 308 increases until the shaft 308 is severed from the screw 302.

At this point, the interface 310 breaks separating the screwdriver shaft 308 from the screw 302 and the screwdriver shaft 308 and the sleeve 312 may be withdrawn from the body. The separation can be steered to some extent by a geometry of the stress riser mentioned above. Thus, the screwdriver assembly 300, similar to the screwdriver assembly 100, utilizes a passive mechanism for the user of the device. The engagement between the screw 302 and the screwdriver shaft 308 is inherent, as they are formed as a single piece, and the disengagement mechanism between the screw 302 and the screwdriver shaft 308 is automatic or near-automatic once the screw 302 has been fully inserted into the bone and resistance to further rotation of the screw 302 provides torque sufficient to break the interface 310.

FIGS. 9-12 show a screwdriver assembly 400 having a cannulated screwdriver body 402 defining a channel 404 along its longitudinal axis sized and shaped to receive a shaft 414 of a rotatable insert 412. The screwdriver 402 has a proximal handle portion 406 for gripping and/or rotating the screwdriver 402 and a distal end 408 sized and shaped to be inserted into a recessed cavity 428 in a head 426 of a screw 424. The channel 404 extends throughout the length of the body 402 and has an internal threaded portion 410 adjacent to the handle 406.

Figure 11:
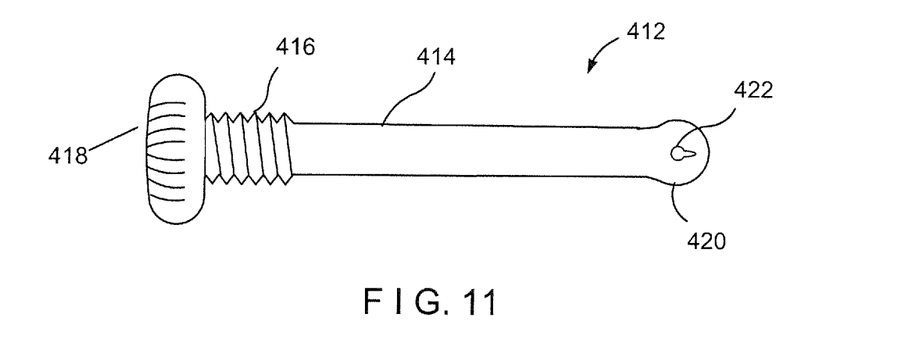
FIG. 11 shows the rotatable insert of the assembly of FIG. 9.

The rotatable insert 412 has a shaft 414 with threaded proximal portion 416 adjacent to a proximal handle 418. At the distal end of the shaft 414 is a deformable tip 420 having a larger cross-section than the shaft 414 and a slot 422 facilitating deformation of the tip 420. When the tip 420 is compressed, it deforms into the slotted area 422 reducing its cross-section to a size at least as thin as the shaft 414. The shaft 414 of the insert 412 is inserted and threaded into the cannulated screwdriver body 402 so that the deformable tip 420 extends out of the distal end 408 thereof and the proximal handle 418 remains proximal to the body 402. The deformable tip 420 may be composed of metallic material, e.g., stainless steel 1.4109, 1.4057, 1.4310, 1.4301, or Custom 465.

Figure 12:
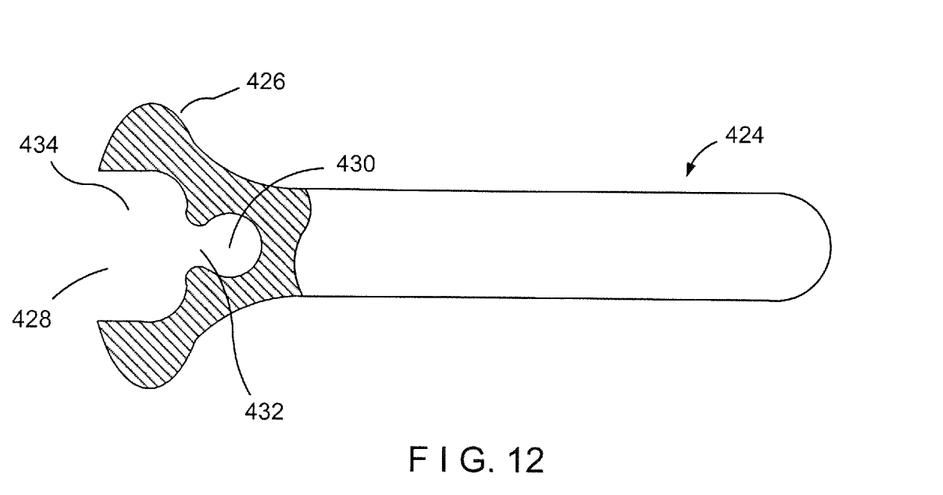
FIG. 12 shows the screw of the assembly of FIG. 9.

The screw 424 includes the head 426 with the recessed cavity 428 therein, the recessed cavity 428 being sized and shaped to receive the distal end 408 of the screwdriver 402, with the deformable tip 420 and a portion of the distal end of the insert shaft 414 extending distally out of the screwdriver 402. In other words, the recessed cavity 428 has a distal-most portion 430 shaped to receive the deformable tip 420 (in a slightly compressed state), an intermediate portion 432 having a reduced diameter to closely fit the insert shaft 414, and a proximal-most portion 434 having an increased diameter to accommodate the distal end 408 of the screwdriver 402.

Figure 9:
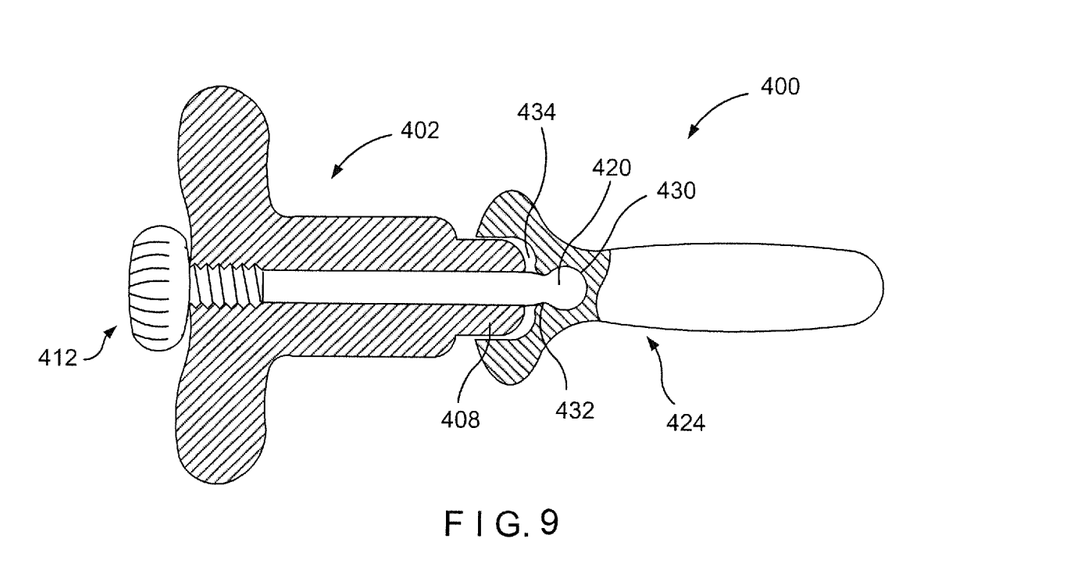
FIG. 9 shows a screwdriver assembly with a cannulated screwdriver body having a rotatable insert according to a third exemplary embodiment.
Figure 10:
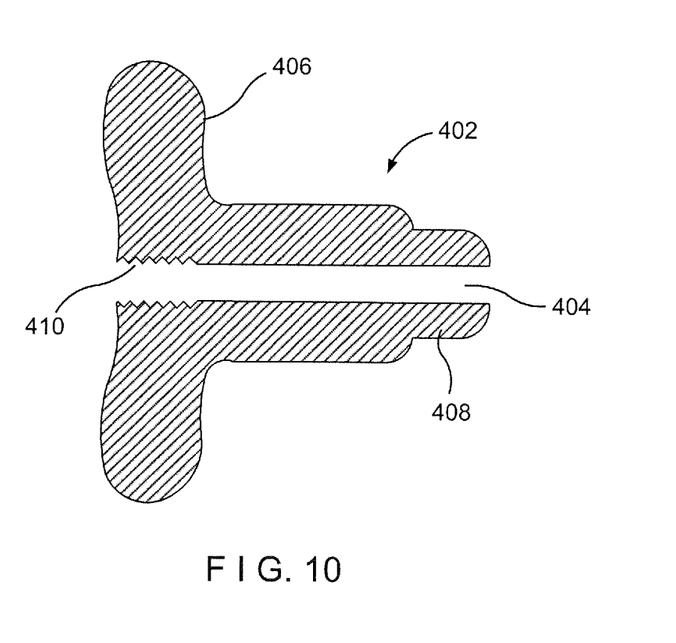
FIG. 10 shows the cannulated screwdriver body of the assembly of FIG. 9.

These elements are pushed distally into the recessed cavity 428, with the deformable tip 420 compressing significantly to get through the reduced diameter section 432, and subsequently expanding slightly when it reaches the distal-most portion 430 with an increased diameter. Mechanical interference between the expanded tip 420 and the reduced diameter intermediate portion 432 prevents inadvertent extraction of the screwdriver 402 from the screw 424. That is, the screw 424 is coupled to the screwdriver 402 until the user provides a force sufficient to again deform the deformable tip 420 and withdraw it from the cavity 428. The distal-most portion 430 of the recessed cavity 428 is sized to be slightly smaller than the undeformed tip 420, such that a radial force is imposed on the inner wall of the distal-most portion 430. Thus, when the assembly 400 is rotated to insert the screw 424, the insert 412 remains in a fixed position relative to the screw 424, i.e., does not rotate and "slip" in the cavity 428.

The combined assembly 400 may be used to insert the screw 424 into the target hole without risk of the screw 424 detaching from the screwdriver. Once inserted, the rotatable insert 412 is detached from the screw 424 by unthreading the threaded proximal portion 416 from the internal threaded portion 410 of the cannulated body 402. The deformable tip 420 will be progressively deformed and drawn through the intermediate portion of the recessed cavity 428 as the elements are unthreaded. Once the deformable tip 420 has proximally cleared the intermediate portion, both the insert 412 and the cannulated body 402 may be withdrawn proximally.

FIGS. 13-17 show a screwdriver assembly 500 with a screwdriver 502 having a cannulated body 501 with a channel 506 along its longitudinal axis sized and shaped to receive an insert shaft 510 of a rotatable insert 508. The screwdriver 502 and the insert 508 are longitudinally fixed at a handle (not pictured), i.e., the elements are coupled so that a distal tip 512 of the insert 508 extends out a distal end of the screwdriver 502, yet the insert 508 and the screwdriver 502 remain rotatable relative to one another. The channel 506 and the corresponding insert shaft 510 are substantially cylindrical so that the screwdriver 502 and the insert 508 may rotate freely relative to one another. However, in this embodiment, the degree of relative rotation between the elements is limited to ~30 degrees by a mechanical stop in the handle, for reasons to be explained below.

Figures 13, 14:
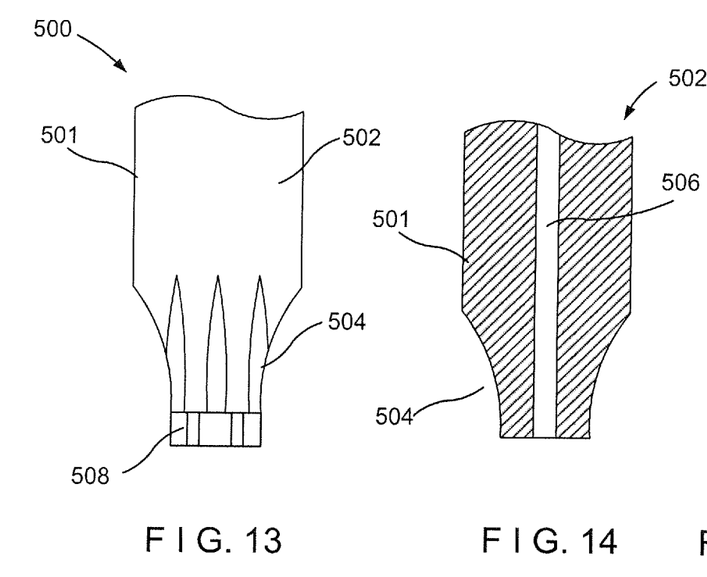
FIG. 13 shows a screwdriver assembly with a cannulated screwdriver body having a rotatable insert according to a fourth exemplary embodiment.
FIG. 14 shows the cannulated screwdriver body of the assembly of FIG. 13.
Figure 15:
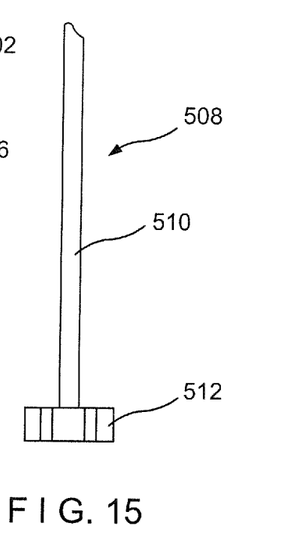
FIG. 15 shows the rotatable insert of the assembly of FIG. 13.
Figure 16:
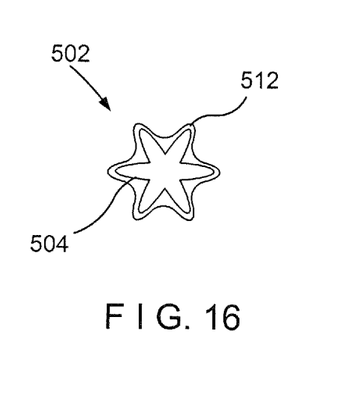
FIG. 16 shows a front view of the rotatable insert and a distal end of the screwdriver of the assembly of FIG. 13.
Figure 17:
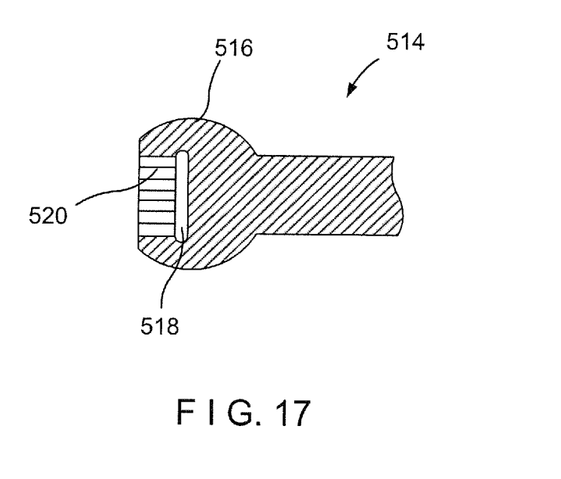
FIG. 17 shows a side section of a screw for use with the assembly of FIG. 13.

The screwdriver 502 has a screwdriver tip 504 distal of the body 501. The screwdriver tip 504 having a hexagonal cross-section, i.e. star shape, having a first diameter (measured between two points of the star). The distal tip 512 of the insert 508 having a similar hexagonal (star-shaped) cross-section, having a second diameter smaller than or equal to the first diameter. A front view of the screwdriver tip 504 being shown in FIG. 16. The distal tip 512 of the insert 508 is sized to pass through a proximal recessed portion 520 of a head 516 of a screw 514 and is sized to engage a distal recessed portion 518 of the head 516. A distal portion of the screwdriver tip 504 mates the proximal recessed portion 520 of the screw 514, the distal portion of the screwdriver tip 504 transmitting the torque required to insert the screw 514 into a pilot hole in the bone.

The screwdriver 502 and the screw 514 are joined and temporarily attached by engaging the distal tip 512 of the insert 508 with the distal recessed portion 518 of the screw head 516. The distal tip 512, although smaller or equal in diameter compared to the distal portion of the screwdriver tip 504, can pass through the proximal recessed portion 520 when the distal tip 512 is oriented so that the grooves are aligned with corresponding ridges in the proximal recessed portion 520. The screwdriver tip 504 follows the distal tip 512 of the insert 508 into the screw head 516 in a same orientation, i.e., so that the points of the star shapes are substantially aligned.

Once the distal tip 512 has been inserted into the distal recessed portion 518 it is rotated relative to the screwdriver 502 and the screw 514 to lock it in place. As mentioned previously, the insert 508 and the screwdriver 502 are rotatable relative to another, but the rotation is limited to, in this embodiment, ~30 deg. When the distal tip 512 is rotated 30 deg (relative to the screwdriver 502 and the screw 514), the points of the star-shaped tip 512 are aligned with the ridges of the star-shaped proximal recessed portion 520 such that the tip 512 cannot be pulled out of the distal recessed portion 518. The distal tip 512 can be removed from the distal recessed portion 518 only by rotating the distal tip 512 back to its original position, i.e., aligned with the screwdriver tip 504.

Once the distal tip 512 has been locked into the distal recessed portion 518, the screwdriver 502 may be rotated to engage the screwdriver tip 504 with the proximal recessed portion 520 and insert the screw 514 into the target hole, while the distal tip 512 remains locked within the distal recessed portion 518 to prevent separation of the screwdriver 502 and the screw 514. After the screw 514 has been fully inserted, the insert 508 may be returned to its initial position relative to the screwdriver 502, i.e., rotated in the opposite direction 30 degrees, so that the points of the respective star shapes align, and separated from the screw 514 so that the screwdriver 502 and the distal tip 512 may be withdrawn from the body.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. A screwdriver assembly, comprising:
a screwdriver shaft extending longitudinally from a proximal end to a distal end and having a longitudinal channel extending therethrough;
an insert having a longitudinal shaft received within the longitudinal channel and a distal end extending distally relative to the distal end of the screwdriver shaft, the insert shaft being rotatable relative to the screwdriver shaft, the distal end of the insert being sized and shaped to engage a head of a screw, the distal end of the insert being disengaged from the screw head by rotating the insert relative to the screwdriver shaft.

2. The screwdriver assembly of claim 1, wherein the distal end of the insert is a deformable tip, a cross-section of the deformable tip being larger than a cross-section of the longitudinal shaft of the insert.

3. The screwdriver assembly of claim 2, wherein the deformable tip has a slot facilitating compression of the deformable tip until a cross-section thereof is at least as small as the cross-section of the longitudinal shaft of the insert.

4. The screwdriver assembly of claim 1, wherein the head of the screw further comprises a cavity, the cavity having a proximal-most portion, an intermediate portion, and a distal-most portion.

5. The screwdriver assembly of claim 4, wherein the proximal-most portion of the cavity is sized and shaped to receive the distal end of the insert, the intermediate portion of the cavity is sized and shaped to receive the longitudinal shaft of the insert, and the distal-most portion of the cavity is sized and shaped to receive the distal end of the screwdriver.

6. The screwdriver assembly of claim 4, further comprising:
a snap lock between the distal end of the insert and the intermediate portion of the cavity to temporarily prevent extraction of the screwdriver from the screw.

7. The assembly of claim 1, further comprising:
a first threaded portion on a proximal portion of the longitudinal channel of the screwdriver; and
a second threaded portion on a proximal portion of the longitudinal shaft of the insert,
wherein the first threaded portion is complementary to the second threaded portion.

8. The screwdriver assembly of claim 1, wherein the head of the screw further comprises:
a proximal recessed portion sized and shaped to receive the distal end of the insert; and
a distal recessed portion sized and shaped to receive the distal end of the screwdriver.

9. The screwdriver assembly of claim 8, wherein the distal end of the screwdriver has a hexagonal shaped cross-section, the cross-section corresponding to a plurality of ridges in the proximal recessed portion.

10. A screwdriver assembly, comprising:
a sleeve with a ridged proximal end and an internally threaded distal end;
a screwdriver having a distal end engageable with the ridged proximal end of the sleeve; and
a screw with an externally threaded head engageable with the distal end of the sleeve, rotation of the assembly inserting the screw into a target hole while the sleeve remains external to the target hole, the rotation of the assembly unthreading the sleeve from the screw so that, when the screw is disengaged from the sleeve, the sleeve remains engaged with the screwdriver and is withdrawn therewith.

11. The screwdriver assembly of claim 10, wherein the sleeve is formed from a flexible material that may elastically deform from an applied force.

12. The screwdriver assembly of claim 10, wherein the screw has a threading extending from a distal end of the threaded head to a distal end of the screw, wherein a length of the externally threaded head corresponds to a length of the threading on the screw.

13. A screwdriver assembly, comprising:
a screwdriver shaft and a screw being formed as a unified piece having an interface therebetween, the interface having a reduced diameter relative to the shaft and the screw; and
a sleeve coupled to the screwdriver shaft at a handle, the screwdriver shaft being rotatable relative to the sleeve to insert the screw into a target hole, the sleeve remaining external to the target hole, rotation of the screwdriver stressing the interface so that the interface breaks when the screw has been inserted into the target hole to a target depth.

14. The screwdriver assembly of claim 13, wherein the sleeve is removably coupleable to the handle, at least one of the sleeve and the handle being reusable.

15. The screwdriver assembly of claim 13, wherein the interface has a shape that creates a stress riser to initiate the interface break between the screw and the shaft.

16. A method, comprising:
inserting a distal end of a screw an initial distance into a target hole in bone, a head of the screw being releasably coupled to a screwdriver, the screwdriver being releasably coupled to a sleeve;
rotating the screwdriver until a distal end of the sleeve engages a surface of the bone surrounding the target hole, preventing the sleeve from rotating with the screw;
advancing the screw distally into the target hole until the screw is completely countersunk into the target hole, disengaging the sleeve from the screw;
interference between the bone and the sleeve prevents rotation of the sleeve until the screwdriver disengages from the screw; and
withdrawing the screwdriver and the sleeve from the bone.

17. The method of claim 16, wherein a breakable interface connects a distal end of the screwdriver to the head of the screw, further comprising disengaging the screwdriver from the screw by breaking the interface.

18. A method, comprising:
inserting a rotatable insert into a channel extending longitudinally through a screwdriver, a distal end of the insert extending past a distal end of the screwdriver;
advancing the distal end of the insert and the distal end of the screwdriver into a head of a screw;
inserting a distal end of the screw an initial distance into a target hole in bone;
rotating the insert relative to the screwdriver to advance the screw distally into the target hole;

disengaging the distal end of the screwdriver and the distal end of the insert from the screw; and withdrawing the screwdriver and the insert from the bone.

19. The method of claim 18, wherein the insert remains in a fixed position relative to the screw when the insert is rotated relative to the screwdriver.

20. The method of claim 18, further comprising:

rotating the insert a predetermined amount in a first direction to prevent separation of the screwdriver and the screw;

advancing the screw distally by rotating the screwdriver; and rotating the insert the predetermined amount in a second direction, the second direction being opposite of the first direction, to allow separation of the screwdriver from the screw.

* * * * *